(12) United States Patent
Abbound et al.

(10) Patent No.: US 7,442,190 B2
(45) Date of Patent: Oct. 28, 2008

(54) CONTACT ASSESSMENT OF BALLOON CATHETERS

(75) Inventors: Marwan Abbound, Pierrefonds (CA); Teresa Ann Mihalik, Montréal (CA); Johnny Al Asmar, Nicosia (CY); Chadi Harmouche, St-Laurent (CA)

(73) Assignee: CryoCath Technologies Inc., Chemin Ste-Marie, Kirkland, Quebec (CA)

( * ) Notice: Subject to any disclaimer, the term of this patent is extended or adjusted under 35 U.S.C. 154(b) by 517 days.

(21) Appl. No.: 11/129,205

(22) Filed: May 13, 2005

(65) Prior Publication Data

US 2006/0259023 A1    Nov. 16, 2006

(51) Int. Cl.
*A61B 18/18* (2006.01)
*A61B 5/02* (2006.01)

(52) U.S. Cl. .................................. 606/21; 600/506
(58) Field of Classification Search ............. 606/20–26, 606/32–35; 607/122; 600/506
See application file for complete search history.

(56) References Cited

U.S. PATENT DOCUMENTS

| | | | |
|---|---|---|---|
| 4,587,975 A * | 5/1986 | Salo et al. ................... 600/506 |
| 5,755,715 A | 5/1998 | Stern et al. |
| 5,971,979 A * | 10/1999 | Joye et al. ..................... 606/21 |
| 6,023,638 A * | 2/2000 | Swanson .................... 600/510 |
| 6,217,573 B1 | 4/2001 | Webster |
| 6,425,877 B1 * | 7/2002 | Edwards ....................... 604/21 |
| 6,514,249 B1 | 2/2003 | Maguire et al. |
| 6,645,202 B1 | 11/2003 | Pless et al. |
| 2004/0199154 A1 * | 10/2004 | Nahon et al. .................. 606/21 |
| 2004/0260328 A1 * | 12/2004 | Zvuloni et al. .............. 606/194 |

\* cited by examiner

*Primary Examiner*—Michael Peffley
(74) *Attorney, Agent, or Firm*—Christopher & Weisberg, P.A.

(57) ABSTRACT

A method and system for determining contact assessment includes the steps of positioning a catheter at a tissue treatment site, where the catheter has a proximal end portion and a distal end portion, the proximal end portion defining at least one fluid inlet port and at least one fluid outlet port, an expandable membrane defining a cooling chamber a coolant injection lumen in fluid communication with the at least one fluid inlet port and the cooling chamber, a coolant return lumen in fluid communication with the at least one fluid outlet port and the cooling chamber, the coolant injection tube, the cooling chamber, and the primary coolant return lumen defining a fluid pathway and a temperature sensor located near the coolant return lumen; measuring an internal temperature of the chamber, and modifying the position of the catheter in response to the measured temperature. The method and system can also use a measured impedance to determine contact assessment.

6 Claims, 2 Drawing Sheets

CONTACT ASSESSMENT OF BALLOON CATHETERS

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates medical systems, and in particular to methods and systems for determining contact assessment.

BACKGROUND OF THE INVENTION

The experimental use of fluids with low operating temperatures, or cryogens, continues in the medical and surgical field. Of particular interest are the potential use of catheter based devices, which employ the flow of cryogenic working fluids therein, to selectively freeze, or "cold-treat", targeted tissues within the body. Catheter based devices are desirable for various medical and surgical applications in that they are relatively non-invasive and allow for precise treatment of localized discrete tissues that are otherwise inaccessible. Catheters may be easily inserted and navigated through the blood vessels and arteries, allowing non-invasive access to areas of the body with relatively little trauma.

Catheter-based ablation systems are known in the art. A cryogenic device uses the energy transfer derived from thermodynamic changes occurring in the flow of a cryogen therethrough to create a net transfer of heat flow from the target tissue to the device, typically achieved by cooling a portion of the device to very low temperature through conductive and convective heat transfer between the cryogen and target tissue. The quality and magnitude of heat transfer is regulated by the device configuration and control of the cryogen flow regime within the device.

A cryogenic device uses the energy transfer derived from thermodynamic changes occurring in the flow of a refrigerant through the device. This energy transfer is then utilized to create a net transfer of heat flow from the target tissue to the device, typically achieved by cooling a portion of the device to very low temperature through conductive and convective heat transfer between the refrigerant and target tissue. The quality and magnitude of heat transfer is regulated by device configuration and control of the refrigerant flow regime within the device.

Structurally, cooling can be achieved through injection of high-pressure refrigerant through an orifice. Upon injection from the orifice, the refrigerant undergoes two primary thermodynamic changes: (i) expanding to low pressure and temperature through positive Joule-Thomson throttling, and (ii) undergoing a phase change from liquid to vapor, thereby absorbing heat of vaporization. The resultant flow of low temperature refrigerant through the device acts to absorb heat from the target tissue and thereby cool the tissue to the desired temperature.

Once refrigerant is injected through an orifice, it may be expanded inside of a closed expansion chamber, which is positioned proximal to the target tissue. Devices with an expandable membrane, such as a balloon, are employed as expansion chambers. In such a device, refrigerant is supplied through a catheter tube into an expandable balloon coupled to such catheter, wherein the refrigerant acts to both: (i) expand the balloon near the target tissue for the purpose of positioning the balloon, and (ii) cool the target tissue proximal to the balloon's thermally-transmissive region to cold-treat adjacent tissue.

During the operation of a medical device in a therapeutic procedure, such as in a blood vessel, the heart or other body organ, the medical user desires to establish a stable and uniform contact between the thermally-transmissive region of the cryogenic device and the tissue to be treated (e.g., ablated). In those instances where the contact between the thermally-transmissive region of the cryogenic device and the tissue to be treated is non-uniform or instable, the resulting ablation or lesion may be less than optimal. It is desirable for the medical professional to assess the state of the contact between the thermally-transmissive region of the cryogenic device and the tissue to be treated, so that appropriate adjustments can be made to re-position the cryogenic device to obtain a more optimal contact and thus a more effective treatment.

It would be desirable to provide an apparatus and method of assessing the quality of the contact between the thermally-transmissive region of the cryogenic device and the tissue to be treated, as well as monitoring and detecting any occurrences of fluid egress.

SUMMARY OF THE INVENTION

The present invention advantageously provides a method and system for tissue contact assessment.

One method for determining contact assessment includes the steps of positioning a catheter at a tissue treatment site, where the catheter has a proximal end portion and a distal end portion, the proximal end portion defining at least one fluid inlet port and at least one fluid outlet port, an expandable membrane defining a cooling chamber a coolant injection lumen in fluid communication with the at least one fluid inlet port and the cooling chamber, a coolant return lumen in fluid communication with the at least one fluid outlet port and the cooling chamber, the coolant injection tube, the cooling chamber, and the primary coolant return lumen defining a fluid pathway and a temperature sensor located near the coolant return lumen; measuring an internal temperature of the chamber, and modifying the position of the catheter in response to the measured temperature.

A catheter having an elongate body defining an injection lumen and an exhaust lumen, an expandable membrane defining a cooling chamber disposed at a point along the elongate body, the cooling chamber in fluid communication with the injection lumen and the exhaust lumen, a first electrode located on the distal side of the expandable member, and a second electrode located on the proximal side of the expandable member.

Another method for determining contact assessment includes the steps of positioning a catheter at a tissue treatment site, where the catheter having an elongate body defining an injection lumen and an exhaust lumen, an expandable membrane defining a cooling chamber disposed at a point along the elongate body, the cooling chamber in fluid communication with the injection lumen and the exhaust lumen, a first electrode located on the distal side of the expandable member, and a second electrode located on the proximal side of the expandable member, injecting an electrical current between the first and second electrodes, measuring an impedance between the first and second electrodes; and, modifying the position of the catheter in response to the measured impedance.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
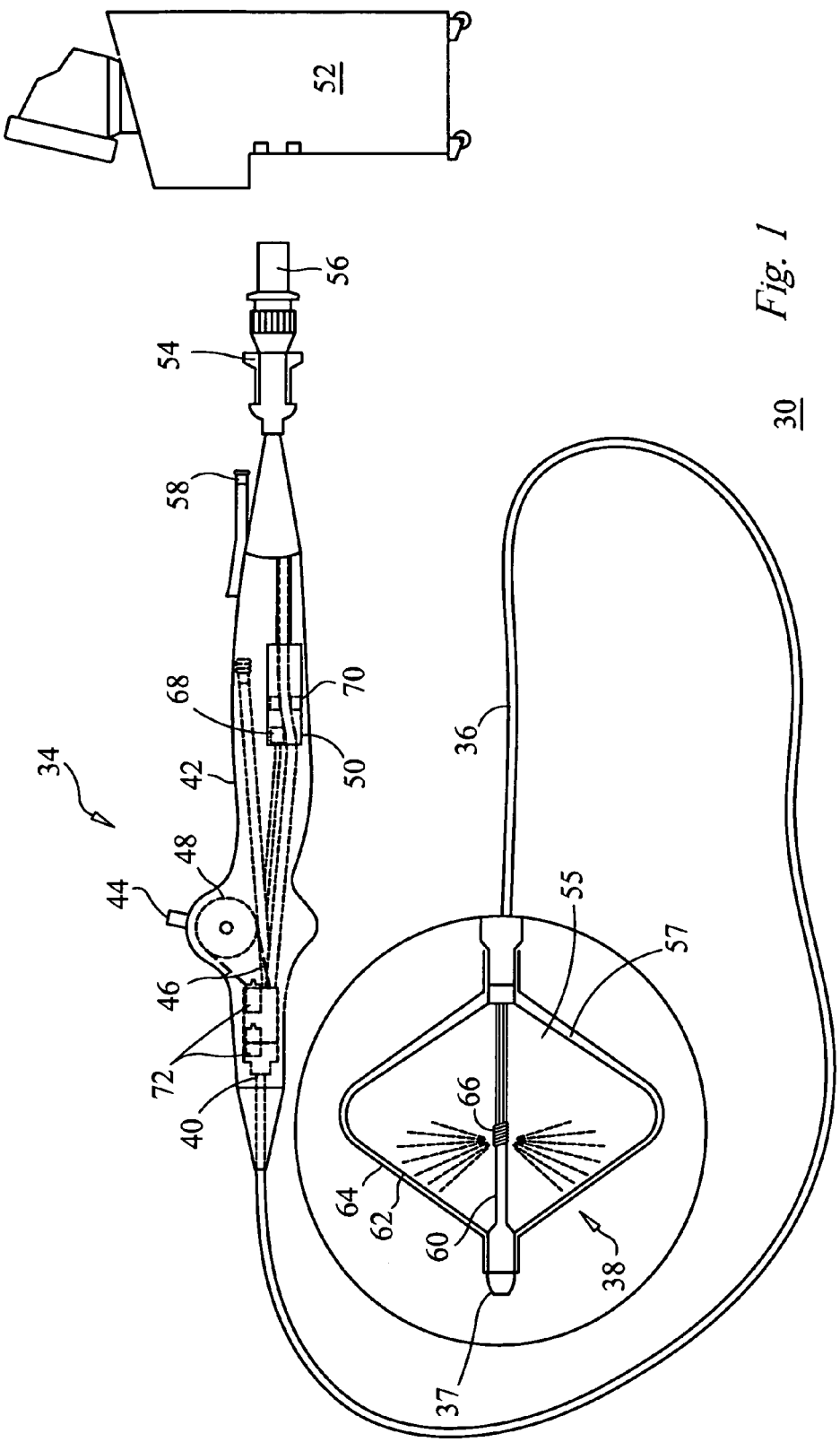
FIG. 1 illustrates a balloon catheter system in accordance with a first embodiment of one aspect of the present invention; and, FIG. 2 illustrates an embodiment of a shaft of the balloon catheter system of FIG. 1.

FIG. 1 illustrates an exemplary system 30 for performing cryogenic ablation. The system 30 includes an elongate, highly flexible ablation catheter 34 that is suitable for passage through the vasculature. The ablation catheter 34 includes a catheter body 36 having a distal end 37 with a thermally conductive element 38 at or proximal to the distal end 37. The distal end 37 and the thermally conductive element 38 are shown magnified and are described in greater detail below. The catheter body 36 has a proximal end 40 that is mated to a handle 42 that can include an element such as a lever 44 or knob for manipulating the catheter body 36 and the thermally conductive element 38. In the exemplary embodiment, a pull wire 46 with a proximal end and a distal end has its distal end anchored to the catheter at or near the distal end 37. The proximal end of the pull wire 46 is anchored to an element such as a cam 48 in communication with and responsive to the lever 44. The handle 42 can further include circuitry 50 for identification and/or use in controlling of the ablation catheter 34 or another component of the system 30.

Continuing to refer to FIG. 1, the handle 42 can also include connectors that are matable directly to a cryogenic fluid supply/exhaust and control unit or indirectly by way of one or more umbilicals. In the system illustrated, the handle 42 is provided with a first connector 54 that is matable with a co-axial fluid umbilical (not shown) and a second connector 56 that is matable with an electrical umbilical (not shown) that can further include an accessory box (not shown). In the exemplary system the fluid supply and exhaust, as well as various control mechanisms for the system are housed in a single console 52. In addition to providing an exhaust function for the ablation catheter fluid supply, the console 52 can also recover and/or re-circulate the cooling fluid. The handle 42 is provided with a fitting 58 for receiving a guide wire (not shown) that is passed into a guide wire lumen 60. During balloon inflation, contrast solution can be injected through the catheter's inner guide wire lumen and into the pulmonary vein.

Still referring to FIG. 1, the thermally conductive element 38 is shown as a double balloon having a first membrane (e.g., inner balloon) 62 contained or enclosed within a second membrane (e.g., outer balloon) 64, thereby defining an interface or junction 57 between the first and second membranes. The second membrane 64 provides a safeguard to prevent fluid from leaking out of the cooling chamber 55 and into surrounding tissue should the first membrane 62, and therefore the cooling chamber 55, rupture or develop a leak. The junction 57 between the first and second membranes 62, 64 may be substantially under a vacuum, such that the first and second membranes 62, 64 are generally in contact with each other, with little or no open space between them. A coolant supply tube 66 in fluid communication with the coolant supply in the console 52 is provided to release coolant from one or more openings in the tube within the inner balloon 62 in response to console commands and other control input. A vacuum pump in the console 52 creates a low-pressure environment in one or more lumens within the catheter body 36 so that coolant is drawn into the lumen(s), away from the inner balloon 62, and towards the proximal end of the catheter body. The vacuum pump is also in fluid communication with the interface or junction 57 of the inner and the outer balloons 62, 64 so that any fluid that leaks from the inner balloon 62 is contained and aspirated. Still referring to FIG. 1, the handle 42 includes one or more pressure sensors 68 to monitor the fluid pressure within one or both of the balloons, the blood detection devices 70 and the pressure relief valves 72. When coolant is released into the inner balloon 62, the inner and the outer balloon 64 expand to a predetermined shape to present an ablation surface, wherein the temperature of the ablation surface is determined by the material properties of the specific coolant selected for use, such as nitrous oxide, along with the pressure within the inner balloon 62 and the coolant flow rate.

Figure 2:
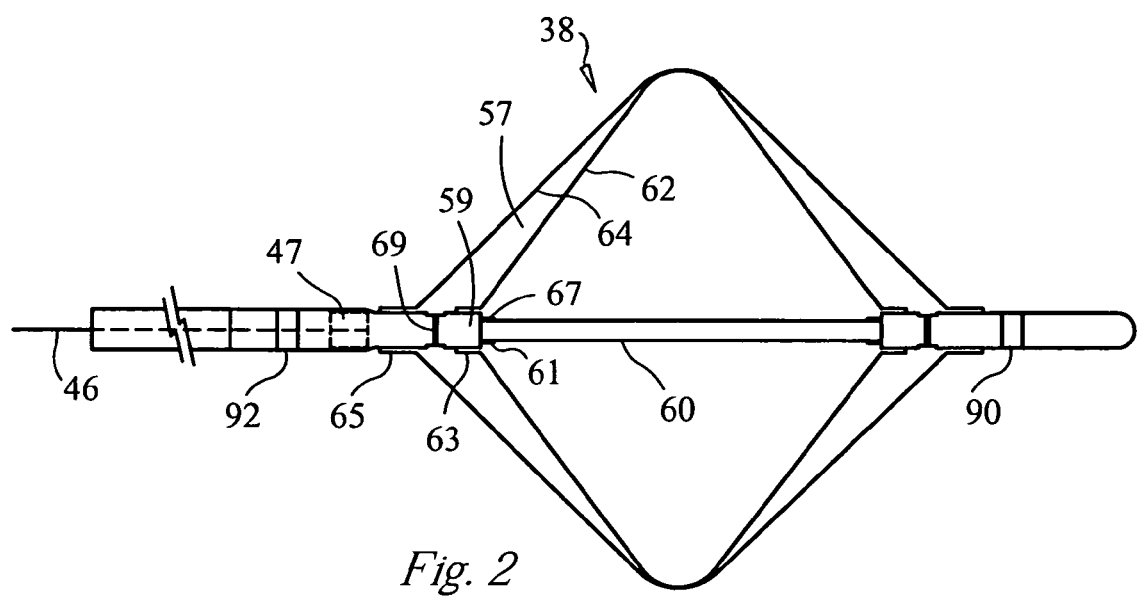

FIG. 2 illustrates an embodiment of a shaft or catheter body 36 of the balloon catheter system 34 of FIG. 1. The catheter body 36 includes a mounting section 59 in communication with the proximal end of thermally conductive element 38. The inner balloon 62 and outer balloon 64 are bonded to the mounting section 59. In this embodiment, the inner balloon 62 and outer balloon 64 are bonded at different locations, which are defined as the inner balloon bond joint 63 and the outer bond joint 65. In addition, several sensors are identified including a temperature sensor 61 (e.g., thermocouple wire), leak detectors 67, 69 (e.g., leak detection wires) and electrodes 90 and 92. In this embodiment, the temperature sensor 61, is positioned at the proximal end of the balloon to measure the coolant flow after the liquid-to-gas expansion. By placing the thermocouple 61 at the proximal end of the balloon near the coolant exhaust, the temperature for the balloon is measured. In those situations where the balloon maintains a stable and uniform contact with the targeted tissue, the temperature of the balloon will remain in the colder region, for example −75 to −90 degrees Celsius. If the balloon is not in a stable and in uniform contact with the targeted tissue, the temperature will be in a warmer region, for example −60 to −75 degrees Celsius. The difference in temperature indicates that there is an incoming blood flow around the balloon (i.e., the balloon is not in uniform contact with the treatment tissue) that causes the balloon temperature to increase because the blood flow acts as a convective heat sink. The control unit 52 can monitor the balloon temperature and provide notification to the operator to terminate the current ablation procedure and reposition the balloon for a more uniform and stable contact with the treatment tissue. There has been an almost high correlation of fluoroscopy-visualized occlusion, inner balloon temperature, and electrical isolation of the pulmonary vein from the left atrium.

In another embodiment, the contact assessment is provided by using the two electrodes 90 and 92 located on each side of the thermally-transmissive region 38 (e.g., a single balloon) and injecting an electrical current between the electrodes while measuring the impedance between the electrodes 90 and 92 with an impedance measurement system 106. Electrical impedance measurement is obtained by passing a current of well-selected amplitude and frequency between two electrodes and measuring the differential voltage as produced across the same electrodes. After injecting a high frequency electrical current to the two electrodes 90, 92, the impedance can be measured by the impedance measurement system 106. The impedance measurement signal is then processed using a signal processor (not shown) that can extract relevant data from a specific frequency range to correlate the impedance change to occlusion of the pulmonary vein. The electrical impedance of the tissue is much higher than the impedance of the blood, so measuring the impedance between the first electrode 90 and the second electrode 92 would indicate the efficacy of a balloon tissue contact. With high measurement sensitivity the system should be able to quantify the contact quality. The impedance measurement system 106 provides information about the baseline impedance that may change as the balloon 38 occludes a vessel, such as a pulmonary vessel (PV). As the balloon will occlude or stop the blood flow between the proximal side and the distal side of the balloon, the impedance at a defined frequency will increase, which provides an indication of the quality of the contact between the balloon 38 and the treatment tissue.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for determining contact assessment comprising:
    positioning a catheter at a tissue treatment site, the catheter comprising:
        a proximal end portion and a distal end portion, the proximal end portion defining at least one fluid inlet port and at least one fluid outlet port;
        an expandable membrane defining a cooling chamber;
        a coolant injection lumen in fluid communication with the at least one fluid inlet port and the cooling chamber;
        a coolant return lumen in fluid communication with the at least one fluid outlet port and the cooling chamber, the coolant injection tube, the cooling chamber, and the primary coolant return lumen defining a fluid pathway; and,
        a temperature sensor located near the coolant return lumen;
    circulating a cryogenic fluid through the catheter;
    measuring an internal temperature of the chamber; and,
    modifying the position of the catheter in response to the measured temperature.

2. The method of claim 1, wherein the catheter is repositioned when the measured temperature is higher than −80 degrees Celsius.

3. The method of claim 1, wherein the catheter is repositioned when the measured temperature is in the range of −60 to −75 degrees Celsius.

4. A method for determining contact assessment comprising:
    positioning a catheter at a tissue treatment site, the catheter comprising:
        an elongate body defining an injection lumen and an exhaust lumen;
        an expandable membrane defining a cooling chamber disposed at a point along the elongate body, the cooling chamber in fluid communication with the injection lumen and the exhaust lumen;
        a first electrode located on the distal side of the expandable member; and
        a second electrode located on the proximal side of the expandable member;
    injecting an electrical current between the first and second electrodes;
    measuring an impedance between the first and second electrodes; and
    assessing contact between the expandable membrane and the tissue treatment site based at least in part on the measured impedance.

5. The method of claim 4, wherein the catheter system further comprises a control unit.

6. The method of claim 4, further comprising modifying the position of the catheter in response to the measured impedance.

* * * * *

UNITED STATES PATENT AND TRADEMARK OFFICE
CERTIFICATE OF CORRECTION

PATENT NO. : 7,442,190 B2  Page 1 of 1
APPLICATION NO. : 11/129205
DATED : October 28, 2008
INVENTOR(S) : Marwan Abboud et al.

It is certified that error appears in the above-identified patent and that said Letters Patent is hereby corrected as shown below:

On the title page item (12), inventor "Marwan Abboud" is incorrectly listed as "Abbound et al." and next to No. (75) Inventors: as "Marwan Abbound".

Please correct the Patent on the title page item (12) as follows:
"Abboud et al."

Please correct the Patent on the title page item (75) Inventors as follows:
"Inventors: Marwan Abboud, Pierrefonds (CA);"

Signed and Sealed this

Twenty-sixth Day of May, 2009

JOHN DOLL
*Acting Director of the United States Patent and Trademark Office*